United States Patent [19]

Atkins et al.

[11] Patent Number: 4,595,754

[45] Date of Patent: Jun. 17, 1986

[54] PROCESS FOR PREPARING CIS N-ALKYLPERHYDROQUINOLINES

[75] Inventors: Randall K. Atkins; Leland O. Weigel, both of Indianapolis, Ind.

[73] Assignee: Eli Lilly and Company, Indianapolis, Ind.

[21] Appl. No.: 707,994

[22] Filed: Mar. 4, 1985

[51] Int. Cl.$^4$ .................. C07D 49/13; C07D 319/08
[52] U.S. Cl. ........................................ 546/18; 549/333
[58] Field of Search .......................... 546/18; 549/333

[56] References Cited

U.S. PATENT DOCUMENTS 4,198,415  4/1980  Kornfeld et al. ................... 424/258

FOREIGN PATENT DOCUMENTS 2140409  11/1984  United Kingdom .

OTHER PUBLICATIONS

Marshall et al., "Reduction of Steroidal Enamines", *J. Org. Chem.*, vol. 28, 421–423, (1963).

Evans et al., "A New Endocyclic Enamine Synthesis" *J.A.C.S.* 92:26, 7593–7595, (1970).
Oppolzer et al., "A Stereoselective . . . Reactions", *Helv. Chim. Acta* 58, 590–593, (1975).
Grob et al., "Synthese . . . -Decahydrochinolinen" *Fasciculus* 4, vol. 48, No. 85, 799–808, (1965).
Kawazoe et al., "Studies on . . . Platinum", *Chem. Pharm. Bull.*, 19(2), 429–432, (1971).
Johnson et al., "The Microbiological . . . Products", *Journal of Organic Chemistry*, vol. 33, No. 8, 3207–3217, (1968).

*Primary Examiner*—Robert T. Bond
*Attorney, Agent, or Firm*—Bruce J. Barclay; Arthur R. Whale

[57] ABSTRACT

A process for preparing a cis N-alkylperhydroquinoline comprising reacting a 3-chloropropyl N-alkylimine with a hydride reducing agent in a basic reaction medium at a temperature in the range of from about −20° C. to about 25° C.

10 Claims, No Drawings

PROCESS FOR PREPARING CIS N-ALKYLPERHYDROQUINOLINES

SUMMARY OF THE INVENTION

The present invention relates to a process for preparing a cis N-alkylperhydroquinoline of the formula

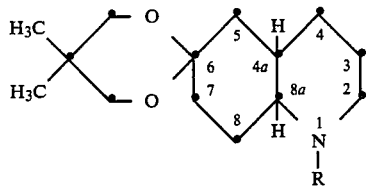

wherein R is $C_1-C_3$ alkyl, comprising reacting a 3-chloropropyl N-alkylimine of the formula

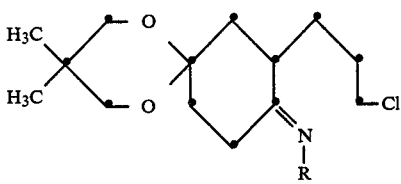

with a hydride reducing agent in the presence of an alcoholic solvent and a basic reaction medium at a temperature in the range of about −20° C. to about 25° C.

The present invention also provides compounds of formula I and formula II as defined above.

DETAILED DESCRIPTION OF THE INVENTION

All temperatures provided herein are in degrees Celsius.

The term $C_1-C_3$ alkyl, as used herein, represents a straight or branched alkyl chain bearing from one to three carbon atoms. $C_1-C_3$ Alkyl groups are methyl, ethyl, n-propyl and isopropyl.

The perhydroquinolines of formula I have two asymmetric centers, one at position 4a and another at position 8a. The compounds thus exist as 4-stereoisomers occurring as two diastereoisomeric pairs or racemates. One diastereoisomeric pair is the Cis racemate, wherein both of the hydrogen atoms at the 4a and 8a positions are on the same side of the plane created by the perhydroquinoline ring. The other diastereoisomeric pair is the trans racemate, wherein the hydrogen atoms at the 4a and 8a positions are on opposite sides in relation to the plane of the perhydroquinoline ring. This invention provides a process for preparing the cis-(±)-racemate which is represented herein as formula I.

This invention also relates to the products of the present process as compounds. Further, this cis racemate may also be resolved to provide the individual cis-(+) and cis-(−) stereoisomers. These two cis stereoisomers may be represented by the following structural formulas:

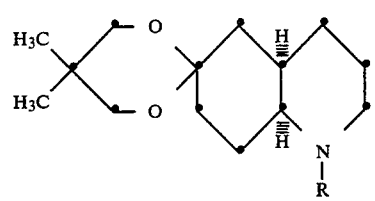

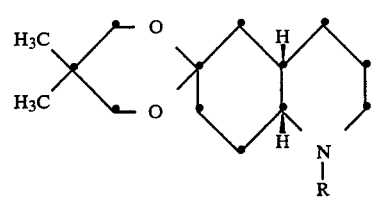

wherein R is as defined above.

Resolution of the cis racemate prepared by the instant process into its optical antipodes can be accomplished by procedures well known to those skilled in the art. These individual stereoisomers are included within the scope of this invention. The cis racemate may be resolved employing any common optically active carboxylic acid known and used for such purposes. Typical resolving agents include tartaric acid, ditoluoyltartaric acid, mandelic acid, malic acid, citric acid, ascorbic acid and other like compounds.

The compounds of formulas I, III and IV, the cis racemate and its individual (+) and (−) stereoisomers, may also exist as acid addition salts. Since the compounds of the invention are basic in nature, they will react with any number of inorganic and organic acids to form salts. Acids commonly used to form acid addition salts of the present invention include hydrochloric, hydrobromic, methanesulfonic, oxalic, phosphoric, p-bromophenylsulfonic, carbonic, succinic, citric, benzoic, acetic and especially p-toluenesulfonic.

The process of the present invention is conducted by combining the 3-chloropropyl N-alkylimine starting material of formula II, or a solution thereof, with a hydride reducing agent in a suitable solvent. The starting material may be dissolved in any one of several non-reactive organic solvents such as diethyl ether, and especially tetrahydrofuran. The hydride reducing agent is combined with an alcoholic solvent such as methanol, ethanol and especially isopropyl alcohol.

The term "hydride reducing agent", as defined herein, refers to any one of several reducing agents capable of selectively reducing the starting material of the present process. Typical reducing agents suitable for use herein include diborane, lithium tri-t-butoxyaluminohydride, lithium aluminum hydride, sodium cyanoborohydride, lithium borohydride, and especially sodium borohydride. The amount of hydride reducing agent employed herein in excess of one mole equivalent of starting material is not critical, but typically from about 1.0 to 2.0 mole equivalents of reducing agent are employed in the present process for each mole equivalent of starting material.

The process is conducted in a basic reaction medium because of the acid labile nature of the starting substrate. Typically the medium will be at a pH in the range of about 8 to 13, more preferably at a pH of about 9 or 10. The basicity of the medium may be generated and maintained by employing the hydride reducing agent as defined above.

The present process is conducted at a temperature in the range of from about −20° C. to about 25° C., more preferably from about 0° C. to about 25° C. When conducted as described herein, the reaction will be substantially complete after about 1 to 24 hours, more specifically from about 1 to 2 hours.

Upon substantial completion of the reaction, the product may be easily isolated by well known procedures. Typically, any excess or residual hydride reducing agent is decomposed by adding a solvent such as acetone to the reaction mixture. The volatiles are then evaporated, generally under reduced pressure, and the residue is dissolved in a water immiscible organic solvent such as methylene chloride, ethyl acetate, toluene, diethyl ether and the like. The organic phase is then normally washed with water and a saturated sodium chloride solution, dried and evaporated to provide the cis N-alkylperhydroquinoline in substantially pure form. The product of the process thus isolated may be further purified, if desired, by any of several routine methods including crystallization from common solvents, chromatography over solid supports such as silica or alumina, and related purification techniques.

The starting materials employed in the present process are readily prepared by known procedures or by procedures analogous to such prior art processes. The preferred process involves reacting 3,3-dimethyl-1,5-dioxaspiro[5.5]undecan-9-one with a (C₁-C₃ alkyl)amine to provide the corresponding N-alkylimine, which is then treated with lithium diisopropylamine (LDA) and 1-chloro-3-iodopropane to afford the starting 3-chloropropyl N-alkylimine starting material of formula II. The scheme for this reaction may be represented by the following:

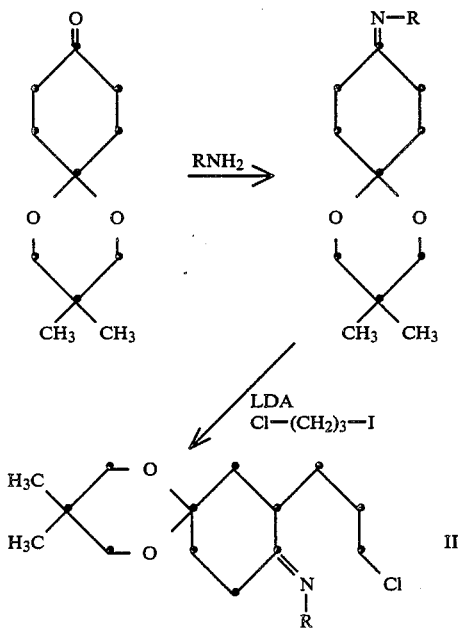

wherein R is as defined above.

The N-alkylimine is prepared by the reaction of 3,3-dimethyl-1,5-dioxaspiro[5.5]undecan-9-one and a primary (C₁-C₃alkyl)amine. The reaction is typically conducted by refluxing the reactants in toluene and in the presence of an acid catalyst such as p-toluenesulfonic acid. A means of removing the water formed as a by-product is also desirable, and generally either molecular sieve, one or more anhydrous inert inorganic salts or a Dean-Stark trap will be employed. The product may then be isolated simply by removing the volatiles under reduced pressure.

The preparation of the 3-chloropropyl N-alkylimine as outlined above from the corresponding imine has been described in general by Evans in *Journal of the American Chemical Society* 92,7593 (1970). More specifically, this reaction involves treating an N-alkylimine with lithium diisopropylamine (prepared by reaction of n-butyllithium and diisopropylamine) at a temperature in the range of −20° C. to about −100° C., more preferably at about −40° C. to −50° C. To this solution is added 1-chloro-3-iodopropane at a temperature in the same range as defined above. The compound is kept from cyclizing to the enamine by maintaining the temperature of the solution below approximately −25° C.

The reactants employed in the process described above are all readily known materials. For example, the compound 3,3-dimethyl-1,5-dioxaspiro[5.5]undecan-9-one is known in the art and commercially available.

The following Example illustrates specific aspects of the present invention. The Example is not intended to be limiting to the scope of the present invention in any respect and should not be so construed.

EXAMPLE 1 cis-Octahydro-5,5-dimethyl-1'-propylspiro[1,3-dioxane-2,6'(2'H)-quinoline]

A.

N-(3,3-Dimethyl-1,5-dioxaspiro[5.5]undec-9-ylidene)-1-propanamine

A 500 ml round bottom flask was charged with 20.32 g (0.103 mol) of 3,3-dimethyl-1,5-dioxazpiro[5.5]undecan-9-one (also known as 1,4-cyclohexanedione mono-2,2-dimethyltrimethylene ketal, from Aldrich Chemical Company, Milwaukee, Wis.), 21.6 g (0.365 mol) of n-propylamine (Eastman Chemical Company, Rochester, N.Y.), 0.01 g of p-toluenesulfonic acid and 100 ml of toluene. The reaction mixture was refluxed for 24 hours with a water separator charged with 16 g of 3-A molecular sieves. The volatiles were removed in vacuo and the residue was held for further synthetic modifications as described below.

B. Lithium diisopropylamine was prepared by combining 10.9 g (0.108 mol) of diisopropylamine and 71.5 ml of 1.51M n-butyllithium in 71 ml of dry tetrahydrofuran at −78° C. The external cooling was removed and the reaction mixture was allowed to stir for one hour until the temperature had reached about 0° C. The mixture was stored at 0° C. for 30 minutes and recooled to −78° C. with a dry ice/acetone bath. The N-(3,3-dimethyl-1,5-dioxaspiro[5.5]undec-9-ylidene)-1-propanamine residue prepared above dissolved in tetrahydrofuran was gradually added to the cold solution of lithium diisopropylamine in 5 ml portions over a 10 minute period. The mixture was allowed to warm to about −30° C. to −25° C. over a period of about 100 minutes. The mixture was held at −30° C. to −25° C. for 20 minutes, recooled to −78° C. and charged with 21.1 g (0.103 mol) of 1-chloro-3-iodopropane. The mixture was allowed to stir at −25° C. and finally held overnight at that temperature. The reaction mixture was poured into a solution of 4.0 g of sodium borohydride and 200 ml of isopropyl alcohol. The reaction became exothermic and was cooled with an ice bath.

The reaction mixture was stirred for two hours and thirty minutes and quenched with 15 ml of acetone. The mixture was allowed to stand overnight. The volatiles were removed under vacuum. The residue was diluted with 500 ml of water and was extracted three times with 200 ml portions of ether. The organic phases were combined, washed with a saturated sodium chloride solution and dried over anhydrous sodium sulfate. The solution was evaporated under vacuum and the residue dried to afford 20.7 g of cis-octahydro-5,5-dimethyl-1'-propyl-spiro[1,3-dioxane-2,6'(2'H)-quinoline]. The structure of the prroduct was verified by NMR.

The compounds prepared by the present process are useful as intermediates to trans octahydropyrazolo[3,4-g]quinolines having utility in the treatment of Parkinsonism and in inhibiting secretion of prolactin.

The products of the present process are converted to the corresponding trans isomers according to procedures well known to those of ordinary skill in the art. This procedure preferably involves reacting the 4-methylbenzenesulfonate salt of a cis N-alkylperhydroquinoline product of the present process with acid to afford the corresponding cis N-alkyl-6-oxoperhydroquinoline salt, which is then converted to the free base and then to the trans N-alkyl-6-hydroxyperhydroquinoline. The scheme for this reaction may be represented by the following:

a water immiscible organic solvent. Exemplary bases for use in this step may be organic or inorganic.

Conversion of the cis perhydroquinoline to the trans perhydroquinoline may also be conducted by procedures known to those of ordinary skill in the art, or by processes analogous to such prior art procedures. Kawazoe et al. in *Chem. Pharm. Bull.* 19(2), 429–432 (1971) disclose the interconversion of cis 1-methyl-decahydroquinoline to the trans isomer employing hydrogenation with Adams' platinum. Accordingly, the present trans isomers may be prepared by dissolving the cis isomer, preferably as the hydrochloride salt, in water and stirring the mixture under a hydrogen atmosphere and in the presence of at least three molar equivalents of platinum catalyst prepared by hydrogenation of platinium oxide. The reaction is complete after about 12 to 72 hours when conducted at a temperature in the range of about 20° C. to about 50° C. The product may be isolated by filtering the reaction mixture through Celite and concentrating the filtrate to dryness under vacuum. The product thus isolated may be further purified by standard techniques if desired.

The foregoing process is used to prepare the trans isomer of the quinoline derivative as defined above. This compound is then converted to the corresponding biologically active octahydropyrazolo[3,4-g]quinoline according to the teaching of U.S. Pat. No. 4,198,415,

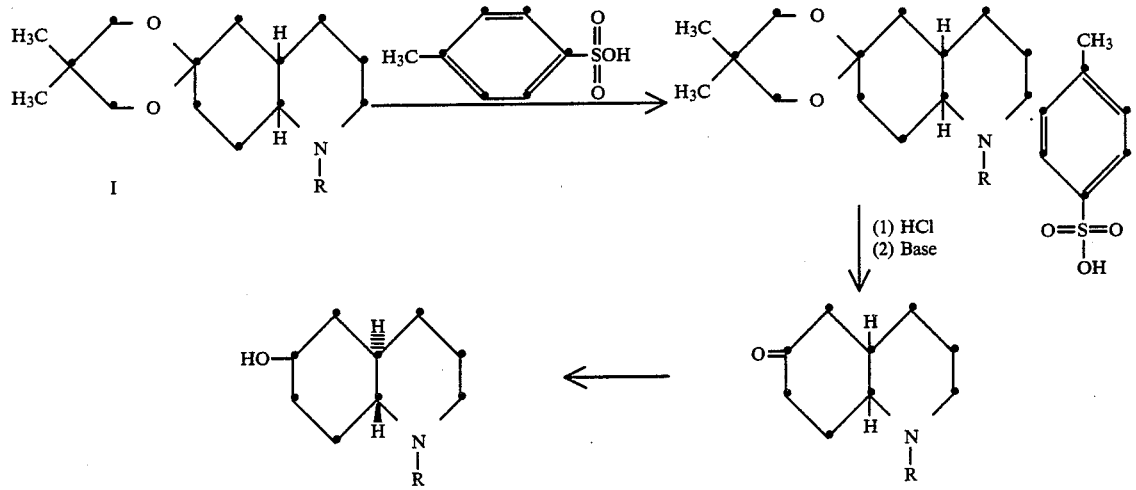

The first step of the above described reaction involves the synthesis of the p-toluenesulfonic acid salt of the perhydroquinoline derivative prepared by the present process. Generally this compound may be prepared simply by combining a solution of about equimolar quantities of the acid and the quinoline, each in a suitable solvent such as methanol or ethanol, at a temperature in the range of about 15° C. to about 150° C. The compound thus prepared may be isolated by evaporation under reduced pressure or collected by filtration.

The synthesis of the cis N-alkyl-6-oxoperhydroquinoline may also be carried out according to procedures well known to those of ordinary skill in the art. Typically the 6-ketal derivative, dissolved in a solvent such as tetrahydrofuran, is hydrolyzed with a suitable acid such as hydrobromic or especially hydrochloric acid. The reaction is typically complete after about 1 to 24 hours when conducted at a temperature in the range of 20° C. to about 150° C. The product is then isolated by adding a base to the reaction mixture and either collecting the precipitated solid or extracting the product with herein incorporated by reference.

The following procedures illustrate the conversion of cis-octahydro-5,5-dimethyl-1'-propylspiro[1,3-dioxane-2,6'(2'H)-quinoline] to the corresponding 4-methylbenzenesulfonate salt, which is hydrolyzed under standard conditions to the 6-keto derivative.

A solution of 12.5 g (0.066 mol) of p-toluenesulfonic acid monohydrate (Aldrich Chemical Co.) in 50 ml of methanol was added to a mixture of 20.7 g (0.079 mol) of cis-octahydro-5,5-dimethyl-1'-propylspiro[1,3-dioxane-2,6'(2'H)-quinoline] dissolved in 50 ml of methanol over a 20 minute period. The reaction flask was cooled with water during the addition of the acid. The mixture was concentrated under reduced pressure and 100 ml of toluene was added to the residue. This procedure was repeated twice until the residue was a solid. The solid was slurried with 200 ml of toluene, and the resulting mixture was cooled to about 10° C. The precipitated solid was collected by filtration, rinsed with 20 ml of toluene and dried to provide 24.2 g of cis-octahydro-5,5-dimethyl-1′-propylspiro[1,3-dioxane-2,6′(2′H)-quinoline]4-methylbenzenesulfonate as a white solid. mp=145°-150° C. dec. Yield 64%.

Analysis calculated for $C_{24}H_{39}NO_5S$. Theory: C, 63.54; H, 8.67; N, 3.09; O, 17.63; S, 7.07. Found: C, 63.81; H, 8.60; N, 3.08; O, 17.41; S, 7.05.

This material appeared to be the cis product by NMR and thin layer chromatography in a 250:50:5 chloroform:methanol:ammonium hydroxide (v:v:v) solvent system.

A second crop of product was obtained from the filtrate to provide 2.17 g of product showing only one spot by thin layer chromatography in the above described solvent system.

A solution of 1.005 g (0.0022 mol) of cis-octahydro-5,5-dimethyl-1′-propylspiro[1,3-dioxane-2,6′-(2′H)-quinoline]4-methylbenzenesulfonate in 5 ml of tetrahydrofuran and 5 ml of deionized water was charged with 8 drops of 12N hydrochloric acid. The reaction mixture was stirred for about 16 hours at about 25° C. and quenched with solid sodium bicarbonate. A thin layer chromatographic analysis of the reaction mixture in a 250:50:5 chloroform:methanol:ammonium hydroxide (v:v:v) solvent system indicated the presence of cis-1-propyl-6-oxooctahydroquinoline.

We claim:

1. A process for preparing a cis N-alkylperhydroquinoline of the formula

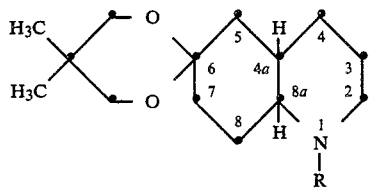

I wherein R is $C_1$–$C_3$ alkyl, comprising reacting a 3-chloropropyl N-alkylamine of the formula

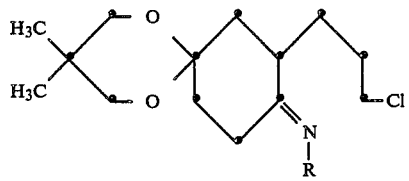

II with a hydride reducing agent in the presence of an alcoholic solvent and a basic reaction medium at a temperature in the range of about −20° C. to about 25° C.

2. A process of claim 1 wherein the hydride reducing agent is sodium borohydride.

3. A process of claim 1 wherein the alcoholic solvent is isopropyl alcohol.

4. A process of claim 1 wherein the reaction is conducted at a temperature in the range of about 0° C. to about 25° C.

5. A process of claim 1 wherein the cis N-alkyldecahydroquinoline is cis-octahydro-5,5-dimethyl-1′-propylspiro[1,3-dioxane-2,6′(2′H)-quinoline].

6. A compound of the formula

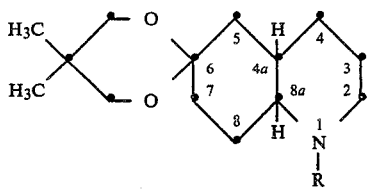

I wherein R is $C_1$–$C_3$ alkyl, or an acid addition salt thereof.

7. The compound of claim 6 which is cis-octahydro-5,5-dimethyl-1′-propylspiro[1,3-dioxane-2,6′(2′H)-quinoline].

8. A compound of the formula

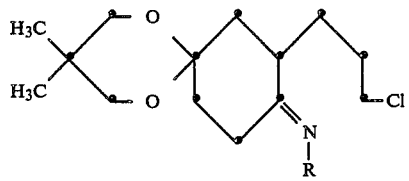

II wherein R is $C_1$–$C_3$ alkyl.

9. A compound of the formula

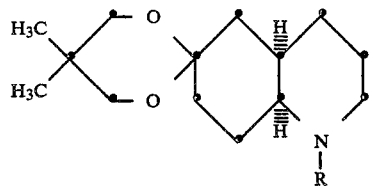

III wherein R is $C_1$–$C_3$ alkyl, or an acid addition salt thereof.

10. A compound of the formula

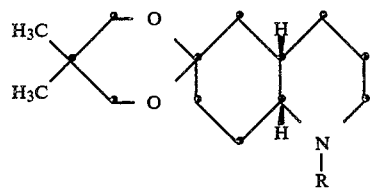

IV wherein R is $C_1$–$C_3$ alkyl, or an acid addition salt thereof.

* * * * *